US009402676B2

United States Patent
Babkin et al.

(10) Patent No.: US 9,402,676 B2
(45) Date of Patent: Aug. 2, 2016

(54) CRYOABLATION BALLOON CATHETER AND RELATED METHOD

(75) Inventors: Alexei Babkin, Albuquerque, NM (US); Peter Littrup, Bloomfield Hills, MI (US); Barron Nydam, Rancho Santa Fe, CA (US); William Nydam, Rancho Santa Fe, CA (US)

(73) Assignee: CryoMedix, LLC, San Diego, CA (US)

( * ) Notice: Subject to any disclaimer, the term of this patent is extended or adjusted under 35 U.S.C. 154(b) by 598 days.

(21) Appl. No.: 13/980,609

(22) PCT Filed: Aug. 26, 2011

(86) PCT No.: PCT/US2011/049287
§ 371 (c)(1),
(2), (4) Date: Jul. 19, 2013

(87) PCT Pub. No.: WO2012/027641
PCT Pub. Date: Mar. 1, 2012

(65) Prior Publication Data
US 2013/0345688 A1 Dec. 26, 2013

Related U.S. Application Data

(60) Provisional application No. 61/377,190, filed on Aug. 26, 2010.

(51) Int. Cl.
*A61B 18/02* (2006.01)
*A61M 25/10* (2013.01)
*A61B 18/00* (2006.01)

(52) U.S. Cl.
CPC ......... *A61B 18/02* (2013.01); *A61B 2018/0022* (2013.01); *A61B 2018/0212* (2013.01); *A61B 2018/0262* (2013.01); *A61M 2025/1086* (2013.01); *A61M 2025/1093* (2013.01)

(58) Field of Classification Search
CPC ........... A61B 18/02; A61B 2018/0212; A61B 2018/0262; A61M 2025/1086; A61M 2025/1093
USPC ...................................... 606/20–26
See application file for complete search history.

(56) References Cited

U.S. PATENT DOCUMENTS 4,249,923 A  2/1981 Walda
4,946,460 A  8/1990 Merry et al.
(Continued)

OTHER PUBLICATIONS

Maybody, et al., Image-Guided Percutaneous Cryoablation of Renal Tumors, Tech Vasc Interventional Rad (2007), vol. 10, pp. 140-148.
(Continued)

*Primary Examiner* — Michael Peffley
*Assistant Examiner* — Khadijeh Vahdat
(74) *Attorney, Agent, or Firm* — Convergent Law Group LLP; Rick Batt

(57) ABSTRACT

Cryoablation balloon catheters and methods are described herein. The cryoablation balloon catheter comprises a distal end section and an inflatable balloon member disposed along the distal end section for contacting a target tissue. The balloon member may be inflated with a thermally conductive liquid. One or more cooling microtubes are positioned within the balloon and a single phase liquid coolant is transported from a liquid source, through the microtubes to the distal section, and returned to a reservoir. Cryogenic energy is transferred from the microtubes, through the conductive liquid filling the balloon, through the wall of the balloon, and to the tissue. In a cryoablation balloon catheter, a plurality of flexible microtubes are adhered to a surface of the expandable balloon. Cryoenergy from the microtubes is directly transferred to the tissue.

15 Claims, 12 Drawing Sheets

(56) References Cited

U.S. PATENT DOCUMENTS

| | | |
|---|---|---|
| 5,207,674 A | 5/1993 | Hamilton |
| 5,305,825 A | 4/1994 | Roehrich et al. |
| 5,334,181 A * | 8/1994 | Rubinsky ............... A61B 18/02 606/20 |
| 5,520,682 A | 5/1996 | Baust et al. |
| 5,573,532 A | 11/1996 | Chang et al. |
| 5,674,218 A | 10/1997 | Rubinsky et al. |
| 5,733,247 A | 3/1998 | Fallon |
| 5,787,715 A | 8/1998 | Dobak, III et al. |
| 5,899,898 A | 5/1999 | Arless et al. |
| 5,946,920 A | 9/1999 | Clarke |
| 5,956,958 A | 9/1999 | Dobak, III et al. |
| 5,978,697 A | 11/1999 | Maytal et al. |
| 6,074,572 A | 6/2000 | Li et al. |
| 6,237,355 B1 | 5/2001 | Li |
| 6,241,722 B1 | 6/2001 | Dobak |
| 6,270,493 B1 | 8/2001 | Lalonde |
| 6,283,959 B1 | 9/2001 | Lalonde et al. |
| 6,355,029 B1 | 3/2002 | Joye et al. |
| 6,471,694 B1 | 10/2002 | Kudaravalli et al. |
| 6,485,422 B1 | 11/2002 | Mikus et al. |
| 6,530,234 B1 | 3/2003 | Dobak, III et al. |
| 6,530,946 B1 | 3/2003 | Noda et al. |
| 6,537,271 B1 | 3/2003 | Murray et al. |
| 6,551,309 B1 | 4/2003 | LePivert |
| 6,679,081 B2 | 1/2004 | Marsala |
| 6,685,720 B1 | 2/2004 | Wu et al. |
| 6,726,653 B2 | 4/2004 | Noda et al. |
| 6,773,408 B1 | 8/2004 | Acker et al. |
| 6,893,433 B2 | 5/2005 | Lentz |
| 6,893,653 B2 | 5/2005 | Abraham et al. |
| 6,904,305 B2 | 6/2005 | Tsekos |
| 6,972,015 B2 | 12/2005 | Joye et al. |
| 6,981,382 B2 | 1/2006 | Lentz et al. |
| 6,984,233 B2 | 1/2006 | Hooven |
| 7,004,936 B2 | 2/2006 | Ryba et al. |
| 7,022,120 B2 | 4/2006 | LaFontaine |
| 4,602,623 A1 | 7/2006 | Allen, Jr. |
| 7,081,111 B2 | 7/2006 | Svaasand et al. |
| 7,192,426 B2 | 3/2007 | Baust et al. |
| 7,220,252 B2 | 5/2007 | Shah |
| 7,648,497 B2 | 1/2010 | Lane |
| 2002/0010460 A1 * | 1/2002 | Joye ....................... A61B 18/02 606/21 |
| 2002/0032438 A1 * | 3/2002 | Lafontaine ............. A61B 18/02 606/21 |
| 2002/0083717 A1 | 7/2002 | Mullens et al. |
| 2002/0115989 A1 | 8/2002 | Abboud et al. |
| 2003/0024250 A1 | 2/2003 | Haas et al. |
| 2003/0055415 A1 | 3/2003 | Yu et al. |
| 2003/0220634 A1 | 11/2003 | Ryba et al. |
| 2004/0215294 A1 | 10/2004 | Littrup et al. |
| 2005/0027334 A1 | 2/2005 | Lentz et al. |
| 2005/0038422 A1 | 2/2005 | Maurice |
| 2005/0182394 A1 | 8/2005 | Spero et al. |
| 2005/0203505 A1 | 9/2005 | Megerman et al. |
| 2005/0261753 A1 | 11/2005 | Littrup et al. |
| 2006/0004349 A1 | 1/2006 | Ryba et al. |
| 2006/0155268 A1 | 7/2006 | Amir et al. |
| 2006/0235375 A1 | 10/2006 | Littrup et al. |
| 2007/0031338 A1 | 2/2007 | Zabinski |
| 2007/0043342 A1 | 2/2007 | Kleinberger |
| 2007/0112251 A1 | 5/2007 | Nakhuda |
| 2007/0119190 A1 | 5/2007 | Yan |
| 2007/0277550 A1 | 12/2007 | Li et al. |
| 2008/0027420 A1 | 1/2008 | Wang et al. |
| 2008/0033419 A1 | 2/2008 | Nields et al. |
| 2008/0114344 A1 | 5/2008 | Xiao et al. |
| 2008/0119834 A1 | 5/2008 | Vancelette et al. |
| 2008/0119839 A1 | 5/2008 | Vancelette et al. |
| 2008/0121759 A1 | 5/2008 | Behrens et al. |
| 2008/0125764 A1 | 5/2008 | Vancelette et al. |
| 2008/0161784 A1 | 7/2008 | Hogan et al. |
| 2009/0234345 A1 | 9/2009 | Hon |
| 2009/0270851 A1 | 10/2009 | Babkin |
| 2009/0287201 A1 | 11/2009 | Lalonde |

OTHER PUBLICATIONS

PCT International Search Report and Written Opinion issued Mar. 27, 2012 for PCT/US2011/049287.

PCT International Search Report and Written Opinion issued May 4, 2010 for PCT/US2009/069046.

PCT International Examination Report issued Oct. 11, 2011 for PCT/US2010/029953.

PCT International Search Report and Written Opinion issued Jan. 26, 2011 for PCT/US2010/033070.

PCT International Search Report and Written Opinion issued May 15, 2012 for PCT/US2011/058094.

* cited by examiner

CRYOABLATION BALLOON CATHETER AND RELATED METHOD

CROSS-REFERENCE TO RELATED APPLICATIONS

The present application claims the benefit of provisional patent application No. 61/377,190 filed Aug. 26, 2010, entitled "An Improved Cryoablation Balloon Catheter with Single Phase Liquid Coolants for Intravascular Applications".

BACKGROUND OF THE INVENTION

This invention relates to cryoablation systems for treating biological tissues, and more particularly, to cryoablation balloon catheters using refrigerants in the liquid state.

Cryoablation therapy involves application of extremely low temperature and complex cooling systems to suitably freeze the target biological tissues to be treated. Many of these systems use cryoprobes or catheters with a particular shape and size designed to contact a selected portion of the tissue without undesirably affecting any adjacent healthy tissue or organ. Extreme freezing is produced with some types of refrigerants that are introduced through the distal end of the cryoprobe. This part of the cryoprobe must be in direct thermal contact with the target biological tissue to be treated.

There are various known cryoablation systems including for example liquid nitrogen and nitrous oxide type systems. Liquid nitrogen has a very desirable low temperature of approximately −200° C., but when it is introduced into the distal freezing zone of the cryoprobe which is in thermal contact with surrounding warm biological tissues, its temperature increases above the boiling temperature (−196° C.) and it evaporates and expands several hundred-fold in volume at atmospheric pressure and rapidly absorbs heat from the distal end of the cryoprobe. This enormous increase in volume results in a "vapor lock" effect when the internal space of the cryoprobe gets "clogged" by the gaseous nitrogen. The associated heat exchanger systems within the cryoprobes are also not compatible with the desired miniature size of probe tips that need to be less than 3 mm in diameter. Additionally, in these systems the gaseous nitrogen is simply rejected directly to the atmosphere during use which produces a cloud of condensate upon exposure to the atmospheric moisture in the operating room and requires frequent refilling or replacement of the liquid nitrogen storage tank.

Nitrous oxide and argon systems typically achieve cooling by expansion of the pressurized gases through a Joule-Thomson expansion element such as a small orifice, throttle, or other type of flow constriction that are disposed at the end tip of the cryoprobe. For example, the typical nitrous oxide system pressurizes the gas to about 5 to 5.5 MPa to reach a temperature of no lower than about −85 to −65° C. at an outlet pressure of about 0.1 MPa. For argon, the temperature of about −160° C. at the same pressure of 0.1 MPa is achieved with an initial pressure of about 21 MPa. The nitrous oxide cooling system is not able to achieve the temperature and cooling power provided by liquid nitrogen systems. Nitrous oxide and Argon-based cooling systems have some advantages because the inlet of high pressure gas at room temperature, when it reaches the Joule-Thompson (JT) throttling component or other expansion device at the probe tip, precludes the need for thermal insulation of its inlet components. However, because of the insufficiently low operating temperature, combined with relatively high initial pressure, cryosurgical applications are strictly limited. Additionally, the Joule-Thomson system typically uses a heat exchanger to cool the incoming high pressure gas using the outgoing expanded gas in order to achieve the necessary drop in temperature by expanding compressed gas. The cold returning gas also requires insulation to avoid freezing nontarget tissues along the course of the cryoprobe from the active tip segment Although an argon system is capable of achieving a desirable cryoablation temperature, argon systems do not provide sufficient cooling power and require very high gas pressures. These limitations are very undesirable because the corresponding probe diameters are currently limited to approximately 1.5 mm OD to allow sufficient high-volume gas flow for JT cooling, which is larger than what is needed for a number of applications.

Another cryoablation system uses a fluid at a near critical or supercritical state. Such cryoablation systems are described in U.S. Pat. Nos. 7,083,612 and 7,273,479. These systems have some advantages over previous systems. The benefits arise from the fluid having a gas-like viscosity. Having operating conditions near the critical point of nitrogen enables the system to avoid the undesirable vapor lock described above while still providing good heat capacity. Additionally, such cryosystems can use small channel probes.

However, challenges arise from use of a near-critical cryogen in a cryoablation system. In particular, there is still a significant density change in nitrogen (about 8 times) once it is crossing its critical point—resulting in the need for long pre-cooling times of the instrument. The heat capacity is high only close to the critical point and the system is very inefficient at higher temperatures requiring long pre-cooling times. Additionally, the system does not warm up (or thaw) the cryoprobe efficiently. Additionally, near-critical cryogen systems require a custom cryogenic pump which is more difficult to create and service.

Still other types of cryosystems are described in the patent literature. U.S. Pat. Nos. 5,957,963; 6,161,543; 6,241,722; 6,767,346; 6,936,045 and International Patent Application No. PCT/US2008/084004, filed Nov. 19, 2008, describe malleable and flexible cryoprobes. Examples of patents describing cryoablation systems for supplying liquid nitrogen, nitrous oxide, argon, krypton, and other cryogens or different combinations thereof combined with Joule-Thomson effect include U.S. Pat. Nos. 5,520,682; 5,787,715; 5,956,958; 6074572; 6,530,234; and 6,981,382.

Various cryo-energy delivering balloon catheters have been described in the patent literature. U.S. Pat. No. 6,736, 809, for example, is directed to a method for treating an aneurysm by cooling a target tissue region of the aneurysm to a temperature below temperature for a preselected time period. The method entails thickening, strengthening, or increasing the density of a blood vessel wall by cooling the blood vessel wall with a cryogenically cooled device. In particular, a device having a heat conductive cooling chamber is disposed proximate to the aneurysm site; and a cryogenic fluid coolant is directed to flow inside the chamber to create endothermic cooling relative to the aneurysm.

U.S. Pat. No. 6,283,959 is also directed to a cryo-energy delivery device. The device described in the '959 patent uses carbon dioxide ($CO_2$) and has a metallic balloon surface with different patterns for greater thermal conductivity. The '959 patent describes use of a non-toxic fluid to fill the balloon such as $CO_2$, or nitrous oxide ($N_2O$), in case of balloon rupture. The '959 patent also describes use of evaporative and JT cooling aspects by injecting a predominant liquid mixture under pressure and allowing evaporation and gas expansion. In addition, these gases are generally functional within the engineering constraints of most balloons and catheters of less than 500 psi pressure. However, with $CO_2$ and $N_2O$ having respective boiling points of −78.5° C. and −88.5° C., it is doubtful that the surface temperatures of a balloon in contact with a vessel wall inside a blood vessel can reach anything lower than approximately −10° C. It is therefore uncertain, or perhaps unlikely, that any of the desired "positive remodeling" needed to keep an artery open to its balloon-dilated extent would be possible since temperatures required to get this stent-like effect need to be less than −40° C.

In addition, if nerve ablation is desired for treating hypertension by ablating the renal nerve adjacent the renal artery, temperatures below −60° C. may be needed for long-term prevention of nerve regrowth and the lasting effects on blood pressure. Therefore, it is uncertain, if not unlikely, that the above described cryo-balloons can achieve the desired temperatures within a biological system because of the physical limitations necessary for evaporative or JT-based cryosystems.

The above mentioned '809 and '959 patents do not describe a design for the generation of sufficiently low temperatures to obtain the desired cryo-physiologic response. Insufficient generation of cold temperatures arise from the physical limitations of the cooling mechanisms, as well as the physical engineering limitations, proposed in the above mentioned patents.

An improved cryoablation balloon catheter that overcomes the above mentioned drawbacks is therefore desirable.

An improved cryoablation balloon catheter that achieves minimal temperatures of less than −40° C. within several millimeters of the balloon surface into adjacent tissue, or vessel wall, is desirable to achieve desired vascular effects from positive remodeling. This is desirable in treating, for example, aneurysms, and to treat hypertension by renal nerve ablation. A cryoablation balloon catheter design is thus desirable that achieves the necessary therapeutic temperatures within the engineering and anatomical constraints.

SUMMARY OF THE INVENTION

A cryoablation balloon catheter for delivering energy to a target tissue comprises an elongate shaft having a distal section. The distal section comprises a cryoenergy delivering core and a first balloon disposed about the energy delivering core. The balloon is inflated with a thermally conductive liquid such that when the balloon is inflated, and the cryoenergy delivering core is activated, cryogenic energy is conducted from the cryoenergy delivering core, through the thermally conductive liquid, through the first wall of the balloon, and to the tissue.

In another embodiment, the cryoenergy delivering core or probe comprises a plurality of microtubes. The thermally conductive liquid may be water or a liquid metal alloy with a melting temperature below 20° C. In another embodiment the conductive liquid is a metal alloy and the metal alloy is the eutectic solution of Gallium and Indium or a combination of Gallium, Indium and Tin.

In another embodiment a pump is provided to inflate the balloon to a pressure of at least 100 psi. A pump or syringe is connected to the catheter to deliver the thermally conductive liquid to the distal section to inflate the first balloon.

In another embodiment, the balloon is preferably a nondistensible balloon. An example of a suitable material for the balloon is a polyimide material. In one embodiment the balloon is folded in the deflated state.

In another embodiment a cryoablation balloon catheter for delivering energy to a target tissue comprises an elongate shaft having a distal section and a first balloon located in the distal section. A plurality of flexible delivery tubes extend lengthwise along a surface of the first balloon. The tubes are for delivering energy to the tissue. At least one return tube extends through the distal section and fluidly couples to the plurality of delivery tubes. The plurality of delivery tubes are preferably fluidly coupled to the at least one return tube such that a liquid coolant flows through the delivery tubes, extracts heat from the tissue, and returns through the at least one return tube completing a liquid flowpath.

In another embodiment the plurality of delivery tubes adhere to an inside surface of the first balloon. In another embodiment the plurality of delivery tubes extend along an outside surface of the first balloon.

In another embodiment of the invention, the cryoablation balloon catheter comprises a plurality of balloon regions circumferentially disposed about the balloon surface. The plurality of flexible delivery tubes comprises a plurality of sets of delivery tubes and each set of the delivery tubes can correspond to one of the balloon regions such that one or more sets of the delivery tubes may be activated to cause region-specific cooling. The regions may be shaped as hemispherical, quarter, eighths, or other fractional type slices or portions.

In another embodiment of the invention a second balloon surrounds or encases the first balloon, forming a gap therebetween. The plurality of delivery tubes may be located within the gap between the first balloon and the second balloon. And the interstitial spaces or gap is filled with a thermally conductive liquid.

A method for delivering cryoenergy comprises the steps of advancing the distal section of a balloon catheter through a lumen and to a target location; inflating the balloon; and sending a single phase liquid coolant along a flowpath through the balloon catheter and to the balloon to extract heat from the tissue. In one embodiment the step of inflating is performed by sending a thermally conductive liquid to the interior of the balloon. The flowpath may be comprised of a plurality of microtubes extending along a surface of the balloon. The microtubes extend along an inside surface of the balloon in one embodiment, and along the outside surface of the balloon in another embodiment.

In another embodiment of the invention, a closed loop, single phase, liquid refrigerant cryoablation balloon catheter system for treating tissue includes a container holding the liquid refrigerant at an initial pressure and initial temperature; a liquid pump; and a cryoablation balloon catheter coupled to the container. The balloon catheter includes a balloon member, and a fluid delivery lumen and a fluid return lumen extending through the elongate shaft and to the balloon member such that the balloon member is in fluid communication with the liquid refrigerant. The balloon catheter is adapted to be expanded when liquid refrigerant is sent into the balloon member, and to be reduced in size when liquid refrigerant is withdrawn from the balloon member. Preferably the return lumen is fluidly coupled to a second container thereby completing the loop of the liquid refrigerant without the liquid refrigerant evaporating as the refrigerant is transported. In another embodiment the container is hand held or portable.

The description, objects and advantages of the present invention will become apparent from the detailed description to follow, together with the accompanying drawings.

BRIEF DESCRIPTION OF THE DRAWINGS

FIG. 4b is an enlarged view of the distal tip shown in FIG. 4a.

FIG. 4c is an enlarged view of the transitional section of the cryoprobe shown in FIG. 4a.

FIG. 4d is an end view of the cryoprobe shown in FIG. 4a.

DETAILED DESCRIPTION OF THE INVENTION

Figure 1:
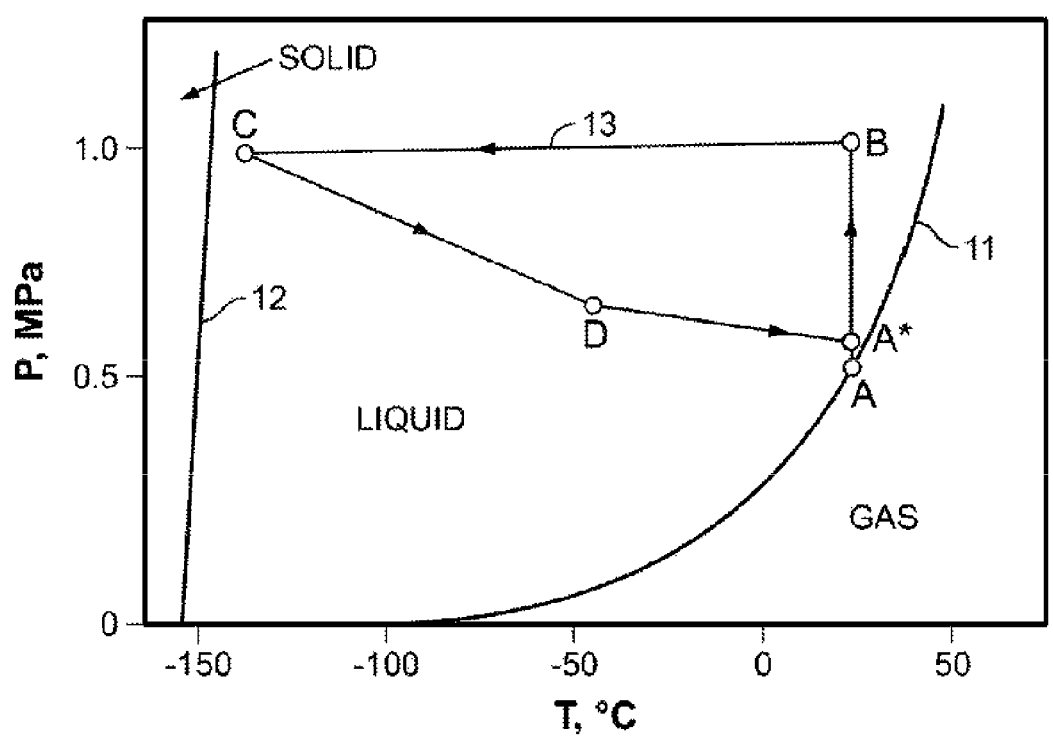
FIG. 1 is a phase diagram corresponding to a cooling cycle of a liquid refrigerant used in a cryoablation system.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

A cooling system for cryoablation treatment uses liquid refrigerants at low pressures and cryogenic temperatures to provide reliable cooling of the distal end of a cryo-apparatus such as, for example, a cryoablation balloon catheter or cryoprobe. The use of liquid refrigerants as the cooling means combined with a multitubular distal end of the cryo-apparatus eliminates the need for refrigerant vaporization and significantly simplifies a cryoablation procedure.

An example of the use of low pressure and cryogenic temperature refrigerants is illustrated in FIG. 1A. In particular, a phase diagram of R218 refrigerant (octafluoropropane) having a melting temperature of about −150° C. is shown. The axes of the diagram in FIG. 1A correspond to pressure P and temperature T of the R218 refrigerant, and include phase lines 11 and 12 that delineate the locus of points (P, T) where solid, liquid and gas states coexist. Although R218 is shown in connection with this embodiment, the invention may include use of other liquid refrigerants.

At point A of FIG. 1A, the refrigerant is in a "liquid-vapor" equilibrium state in a storage tank or container. It has a temperature $T_o$ of the environment, or slightly lower, at an initial pressure $P_0$ of about 0.4 MPa. The closed loop cycle or refrigerant flowpath begins at the point where the liquid refrigerant exits the container or storage tank. In order for the refrigerant to remain in the liquid state throughout the entire cooling cycle and provide necessary pressure for the cryogen to flow through a cryoprobe or a catheter it is maintained at a slightly elevated pressure in the range from about 0.7 to 1.0 MPa (or in this example about 0.9 MPa). This corresponds to point B of FIG. 1A. Point B is in the liquid area of R218 refrigerant. Further, the liquid is cooled by a cooling device (such as but not limited to a refrigerator) from point B to point C to a temperature $T_{min}$ that is shown by path 13 in FIG. 1A. This temperature will be somewhat higher (warmer) than its freezing temperature at elevated pressure.

The cold liquid refrigerant at point C is used for cryoablation treatment and directed into the distal end of the cryodevice that is in thermal contact with the biological tissue to be treated. This thermal contact results in to a temperature increase of the liquid refrigerant with a simultaneous pressure drop from point C to point D caused by the hydraulic resistance (impedance) of the microchannel distal end of the cryoprobe. The temperature of the return liquid is increased due to its environment. In particular, the temperature is increased due to thermal communication with the ambient surroundings and by slightly elevated pressure maintained by a device, e.g., a check valve (point A*). A small pressure drop of about 6 kPa is desirable to maintain the liquid phase conditions in a return line that returns the liquid refrigerant back to the storage tank. Finally, the cycle or flowpath is completed at the point where the liquid cryogen enters the storage tank. Re-entry of the liquid refrigerant may be through a port or entry hole in the container corresponding once again to point A of FIG. 1A. The above described cooling cycle may be continuously repeated as desired.

Refrigerators such as, for example, a Pulse Tube Refrigerator (PTR) having a temperature regulating device can be used to cool the liquid.

Figure 2:
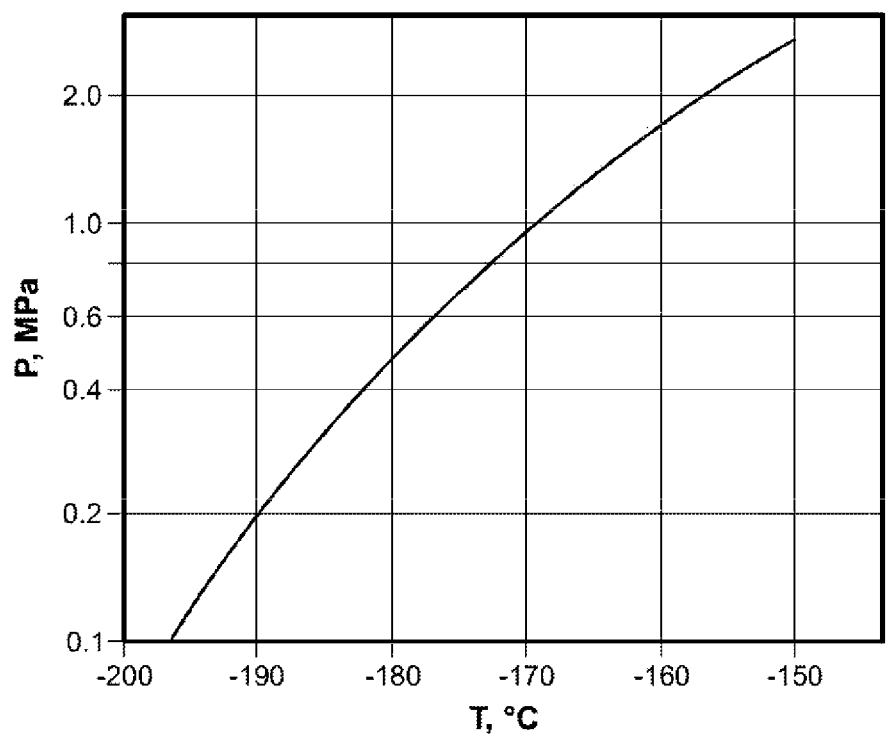
FIG. 2 is a diagram of the boiling temperature of liquid nitrogen as a function of pressure.

In some examples the cooling device or refrigerator can be a heat exchanger submerged in pressurized liquid nitrogen having a predetermined temperature $T_{min}$ depending on its pressure. The pressure may range from about 1.0 to 3.0 MPa. The liquid nitrogen can be replaced by liquid argon or krypton. In these cases, the predetermined temperatures $T_{min}$ will be obtained at pressures as low as about 0.1 to 0.7 MPa. An example of a "pressure, P-temperature, T" diagram of liquid nitrogen is shown in FIG. 2 defining the necessary predetermined temperature $T_{min}$ and corresponding pressure of the liquid refrigerant.

Figure 3A:
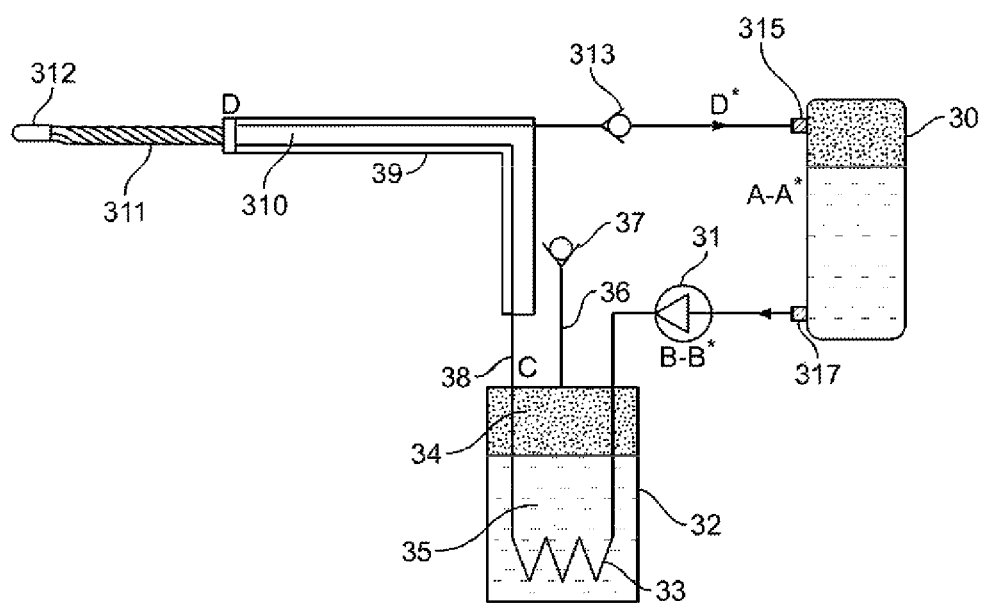
FIGS. 3A-3C are schematic representations of various types of cryoablation systems.

A cooling system for cryoablation treatment is schematically shown in FIG. 3A where the liquid refrigerant at initial pressure $P_0$ in container 30 is compressed by a liquid pump 31 under temperature $T_0$ of the environment. Contrary to typical closed cooling cycles where cooling is achieved by evaporating refrigerants followed by high compression of the vapor, this pump can be very small in size as it drives the incompressible liquid.

Further, the liquid refrigerant is transferred into the refrigerator 32 through the coiled portion 33 which is submerged in the boil-off cryogen 34, 35 provided by transfer line 36 and maintained under a predetermined pressure by check valve 37.

The boil-off cryogen has a predetermined temperature $T_{min}$. The coiled portion 33 of the refrigerator 32 is fluidly connected with multi-tubular inlet fluid transfer microtubes of the flexible distal end 311, so that the cold liquid refrigerant having the lowest operational temperature $T_{min}$ flows into the distal end 311 of the cryoprobe through cold input line 38 that is encapsulated by a vacuum shell 39 forming a vacuum space 310. The end cap 312 positioned at the ends of the fluid transfer microtubes provides fluid transfer from the inlet fluid transfer microtubes to the outlet fluid transfer microtubes containing the returned liquid refrigerant. The returned liquid refrigerant then passes through a check valve 313 intended to decrease the pressure of the returned refrigerant to slightly above the initial pressure $p_0$. Finally, the refrigerant re-enters the container 30 through a port or opening 315 completing the flowpath of the liquid refrigerant. The system provides continuous flow of a refrigerant, and the path A-B-C-D-A*-A in FIG. 3A corresponds to phase physical positions indicated in FIG. 1A. The refrigerant maintains its liquid state along the entire flowpath or cycle from the point it leaves the container through opening 317 to the point it returns to the storage tank or container via opening 315.

An example of a closed loop cryoprobe using a liquid refrigerant is described in patent application Ser. No. 12/425, 938, filed Apr. 17, 2009, and entitled "Method and System for Cryoablation Treatment".

Preferably, the minimum achievable temperature $T_{min}$ of the described process is not to be lower than the freezing temperature of the liquid refrigerants to be used. For many practical applications in cryosurgery, the temperature of the distal end of the cryoprobe must be at least −100° C. or lower, and more preferably −140° C. or lower in order to perform a cryoablation procedure effectively. Non-limiting examples of non-toxic liquid refrigerants for use with the present invention are set forth in table 1 below. These have normal freezing temperatures at about −150° C. or lower.

TABLE 1

| Refrigerant | Chemical formula | Molecular mass (kg/mol) | Normal freezing point (° C.) |
|---|---|---|---|
| R218 | $C_3F_8$ | 188.02 | −153 |
| R124 | $C_2HClF_4$ | 136.5 | −199 |
| R290 | $C_3H_8$ | 44.1 | −187 |
| R1270 | $C_3H_6$ | 42.08 | −185 |
| R600A | i-$C_4H_{10}$ | 58.12 | −160 |

Figure 3B:
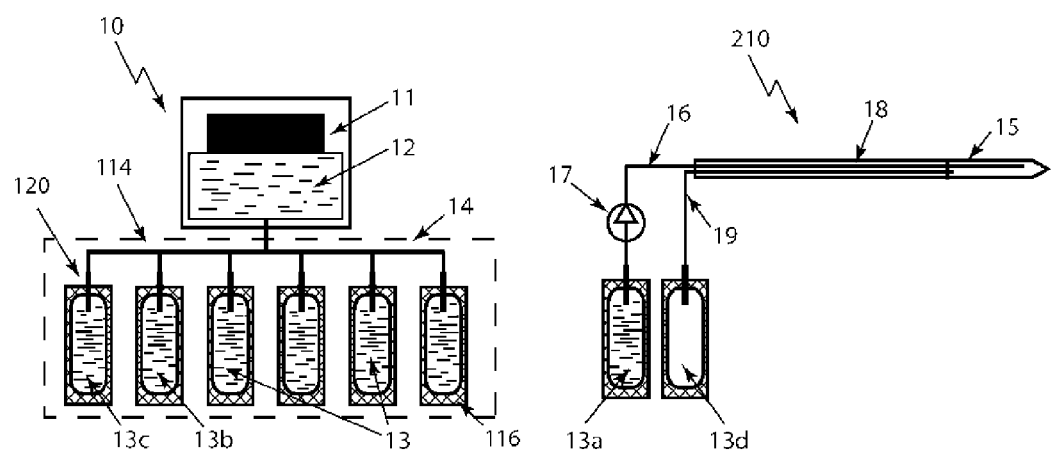
Figure 3C:
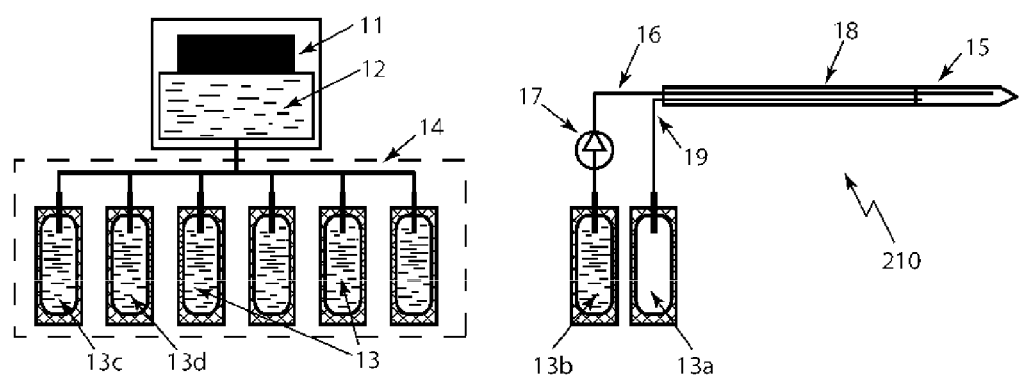

The cryogenic delivery container may also be designed as a hand held mini-container with a protective insulating shell as shown in FIGS. 3B-3C. Cryogenic containers may be arranged as several cartridges. For example, and with reference to FIG. 3B, the cold liquid refrigerant 12 may be delivered to the thermally insulated cryogenic containers 13b, 13c placed in docking station which may be in the form of a chamber 14. The containers are fluidly connected to the refrigerator via a refrigerator line 114. Each of the containers 13 has a connector 120 for detachably fluidly connecting to the refrigerator line 114. The line 114 in some instances may include two or more lumens to deliver fresh chilled liquid and remove warmer liquid. The line is connected to the container. An example of a connector is a fluid tight threaded nipple. However, other means of connectors may be used.

FIG. 3B also shows a container 13a, 13d installed in fluid communication with the cryoprobe 210. In particular, inlet line 16 of the cryoprobe is fluidly connected to container 13a. A liquid pump 17 is positioned along the refrigerant flowpath to pressurize the liquid refrigerant, driving the liquid refrigerant from the container 13a to the cryoprobe tip section 15. In other embodiments the pump can be placed in other locations within the 210 system. Return line 19 transports the liquid refrigerant from the distal section 15 towards the proximal end of the probe and ultimately to an empty receiver container 13d.

FIG. 3B also shows cryoprobe having an insulation 18. The insulation 18 surrounds the inlet line 16 and return line 19 to thermally insulate them from causing thermal damage to the surrounding healthy tissues. Insulation 18 may be in the form of a vacuum shell or another type of insulation such as a coating having a low coefficient of thermal conductivity.

The discharged cryogenic container 13a is disconnected from the inlet line 16 shown in FIG. 3B and connected to return line 19 of the cryoprobe 210 shown in FIG. 3C. Container 13d, which has been filled with warmer discharged liquid refrigerant from the cryoprobe is placed or docked in chamber 14. Newly charged cryogenic container 13b is then connected with inlet line 16 and becomes a cryogenic delivery container as shown in FIG. 3C.

In this manner, each of the containers 13a,b,c,d may be charged, spent (or used), refilled, and returned to the docking station in a convenient, interchangeable manner. The containers shown in this embodiment are identical in shape and size.

Further details of a SPLC system using a docking station and portable containers is described in U.S. patent application Ser. No. 12/770,572, filed Apr. 29, 2010.

Figure 4A:
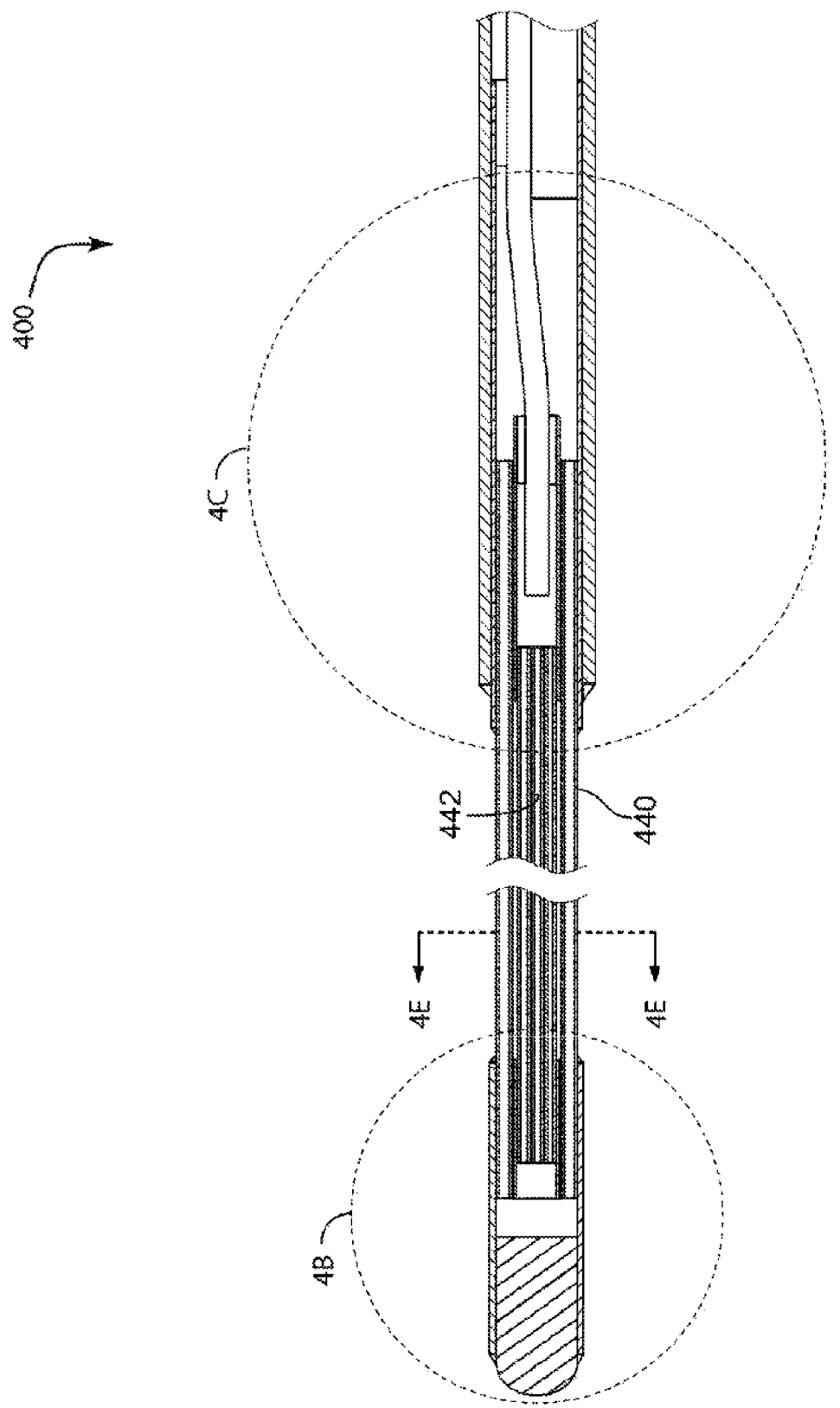
FIG. 4a is a cross sectional view of a distal section of a cryoprobe.

Referring to the FIG. 4a, a distal section 400 of a cryoprobe is shown. The distal section 400 includes a cryoenergy-delivery core section made up of a plurality of tubes 440, 442.

Figure 4B:
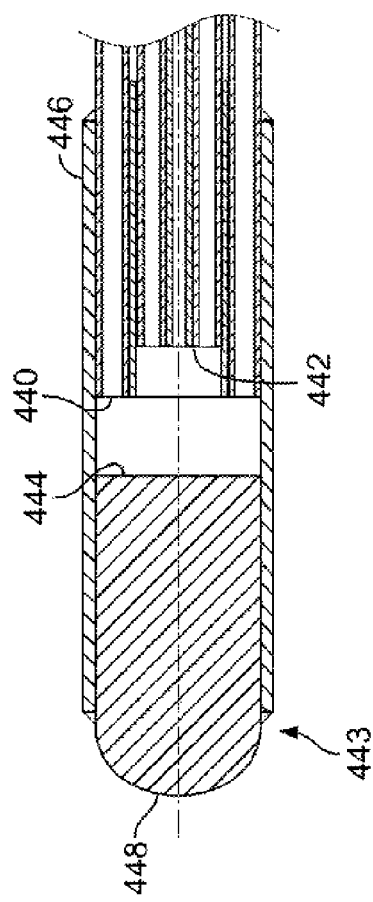
Figure 4C:
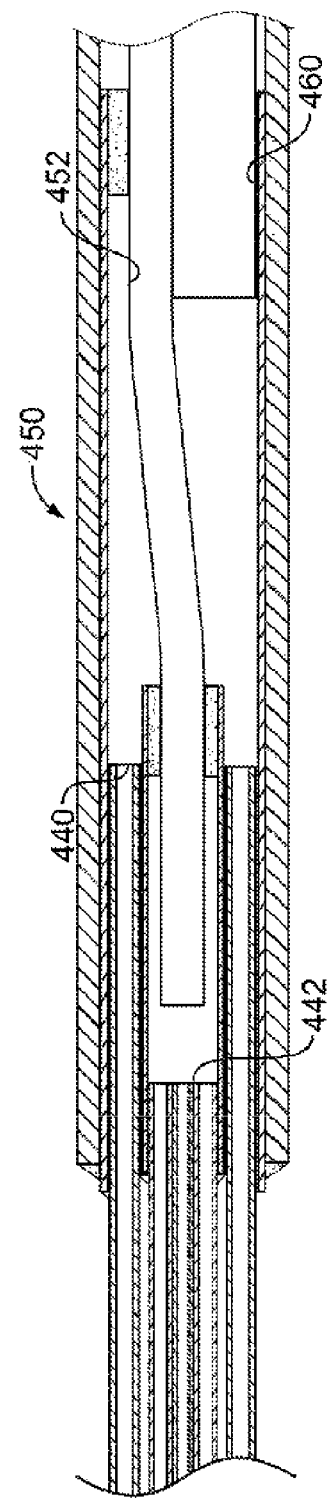
Figure 4D:
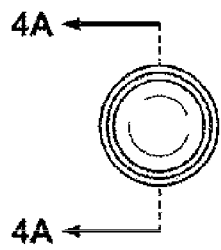
Figure 4E:
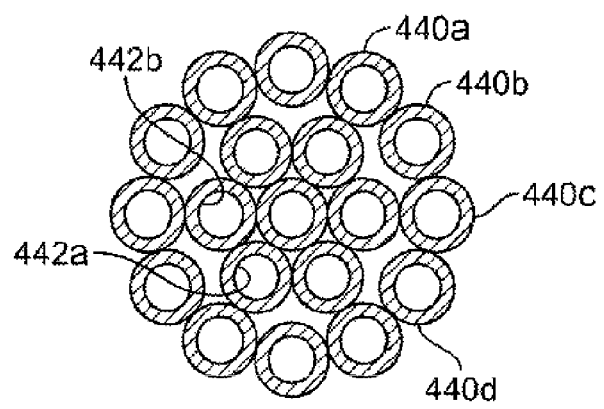
FIG. 4e is a cross sectional view taken along line 4e-4e illustrating a plurality of microtubes for transporting the liquid refrigerant to and from the distal tip of the cryoprobe.

With reference to FIG. 4c and FIG. 4e, the distal section 400 includes two sets of tubes: inlet fluid transfer microtubes 440 and outlet fluid transfer microtubes 442. The inlet fluid transfer tubes 440 direct liquid refrigerant to the distal section of the cryoprobe creating a cryogenic energy delivering region (or core) to treat tissue in the vicinity of the probe. These cooling (or active) microtubes are shown in an annular formation. The outlet fluid transfer (or return) microtubes 442 direct liquid refrigerant away from the target site.

FIG. 4b is an enlarged view of the distal end of energy delivering section 400 shown in FIG. 4a. An end cap 443 is positioned at the ends of the inlet microtubes 440 and outlet microtubes 442, defining a fluid transition chamber 444. The transition chamber 444 provides a fluid tight connection between the inlet fluid transfer microtubes and the outlet fluid transfer microtubes. The end cap may be secured and fluidly sealed with an adhesive or glue. In one embodiment, a bushing 446 is used to attach plug 448 to the distal section. Other manufacturing techniques may be employed to make and interconnect the components and are still intended to be within the scope of the invention.

FIG. 4c illustrates an enlarged view of a transitional region 450 in which the plurality of cooling microtubes 440 are fluidly coupled to one or more larger inlet passageways 460 and the return microtubes are fluidly coupled to one or more larger return passageways 452. The return line(s) ultimately direct the liquid refrigerant back to the cryogen source or container such as, for example, container 30 described in FIG. 3A above, and thereby complete the flowpath or loop of the liquid cryogen and without allowing the cryogen to evaporate or escape.

The inlet line 460 may be thermally insulated. Insulation may be carried out with coatings, and layers formed of insulating materials. A preferred insulating configuration comprises providing an evacuated space, namely, a vacuum layer, surrounding the inlet line.

The fluid transfer microtubes may be formed of various materials. Suitable materials for rigid microtubes include annealed stainless steel. Suitable materials for flexible microtubes include but are not limited to polyimide (e.g., Kapton® polyimide from DuPont). Flexible, as used herein, is intended to refer to the ability of the multi-tubular distal end of the cryoprobe to be bent in the orientation desired by the user without applying excess force and without fracturing or resulting in significant performance degradation. This serves to manipulate the distal section of the cryoprobe about a curved tissue structure.

Flexible microtubes may be formed of a material that maintains flexibility in a full range of temperatures from −200° C. to ambient temperature. Materials may be selected that maintain flexibility in a range of temperature from −200° C. to 100° C. One example of such material is polyimide.

The dimensions of the fluid transfer microtubes may vary. Each of the fluid transfer microtubes preferably has an inner diameter in a range of between about 0.05 mm and 2.0 mm and more preferably between about 0.1 mm and 1 mm, and most preferably between about 0.2 mm and 0.5 mm. Each fluid transfer microtube preferably has a wall thickness in a range of between about 0.01 mm and 0.3 mm and more preferably between about 0.02 mm and 0.1 mm.

Ice shapes may be formed about the multi-tubular distal end of cryoprobe. The ice shape can be created in a desired form by bending the distal end in the desired orientation including, e.g., a curve, arc, or complete loop. The flexible multitubular probe allows for complex bending motion including complete loops to be formed. Further details of a cryoablation multitube probe are described in U.S. patent application Ser. No. 12/754,457, filed Apr. 4, 2010.

Figure 5A:
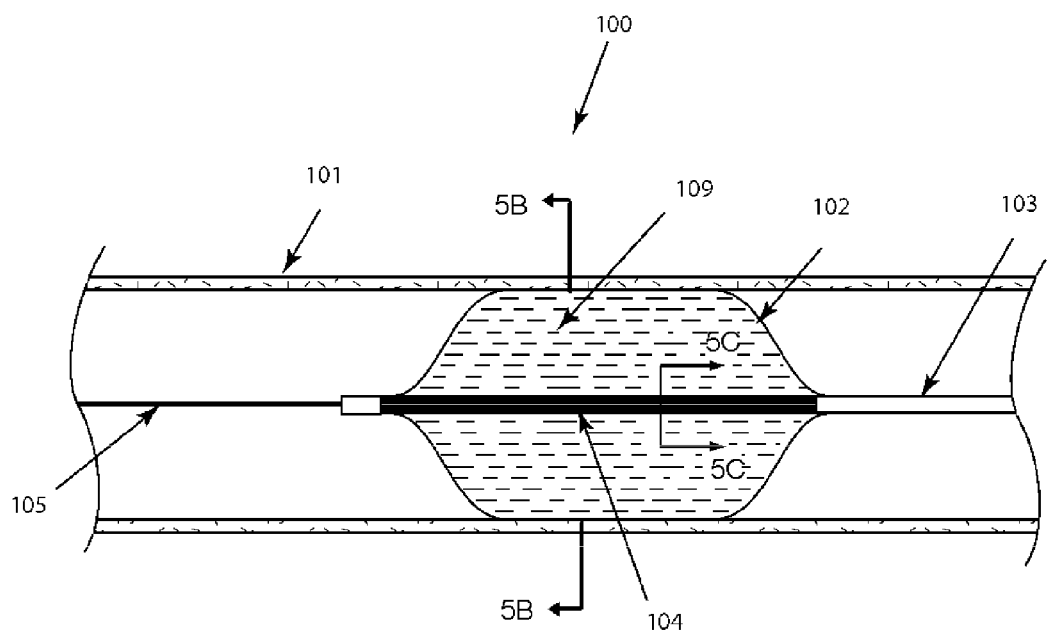
FIG. 5A is an illustration of a cryoablation balloon catheter inside a lumen.
Figure 5B:
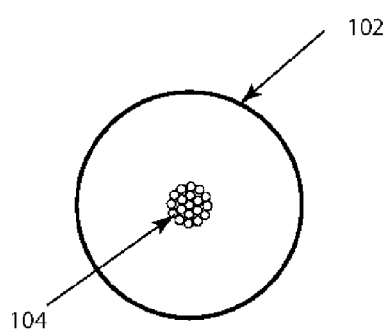
FIG. 5B is a cross sectional view corresponding to the plane 5B-5B of the inflated balloon of the catheter shown in FIG. 5A.
Figure 5C:
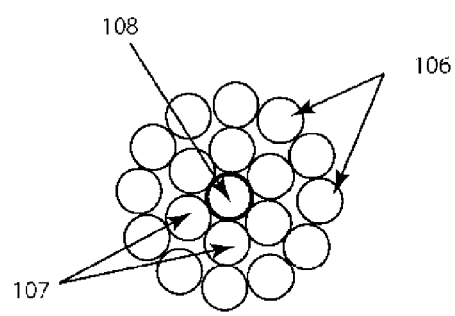
FIG. 5C is a cross sectional view corresponding to the plane 5C-5C of the inflated balloon of the catheter shown in FIG. 5A.

With reference to FIG. 5A, a cryoablation balloon catheter 100 is shown in a lumen 101 such as a blood vessel, airway, or other tubular organ. Catheter may be advanced to a particular location along the lumen via manipulating the proximal end of the catheter as is known to those of ordinary skill in the art. In one embodiment, and as shown in FIG. 5A, catheter 100 is disposed over a guidewire 105. A guidewire lumen 108 as shown in FIG. 5C is sized to slideably receive a guidewire. However, it is to be understood that the invention is not so limited as to require a guidewire except where explicitly recited in the claims.

As shown in FIG. 5A, the distal section of the catheter comprises a balloon 102. The balloon 102 encases or surrounds one or more cryotubes 104. Preferably, balloon catheter 100 includes a plurality of delivery tubes 106 and return tubes 107 in a concentric arrangement as shown in FIG. 5B, 5C. The delivery tubes 106 are shown on the outer perimeter of bundle 104, concentrically surrounding, return tubes 107. Though the microtubes are shown in a particular arrangement, their order or arrangement may vary. For example the microtubes may also be disposed in a weave, braid, or twisted bundle.

Figure 5D:
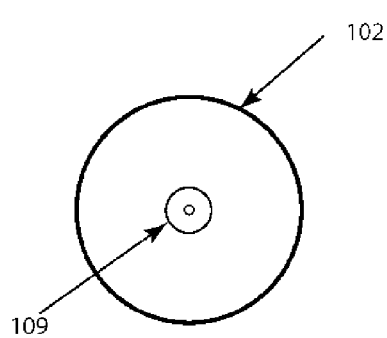
FIG. 5D is a cross sectional view of an alternative balloon catheter design taken along 5B-5B.

FIG. 5D shows another balloon catheter design and in particular, a cryoenergy core having only one lumen for delivering the cryogen to the tip, and one return lumen for returning the cryogen. The balloon catheter, although not shown, may also have a guide wire channel 108 similar to that shown in FIG. 5C.

The balloon may be attached to the distal section of the catheter using adhesive, heat, or another technique. In one embodiment, a bushing is used to attach balloon to the distal section. Other manufacturing techniques may be employed to make and interconnect the components and are still intended to be within the scope of the invention.

Balloon or sheath 102 may be inflated with a fluid 109 such as a thermally conducting liquid, gel, superfluid, gas, or metal that does not exceed the upper pressure limit of balloon catheters. Examples of thermally conducting liquids include but are not limited to water and a non-toxic salt solution such as, e.g., saline at 0.9% sodium chloride.

A fluid inflation lumen extending through the catheter includes at least one distal port in fluid communication with the balloon. The fluid inflation lumen also includes a proximal port for receiving the fluid. For example, a proximal port of the fluid inflation lumen may be connected to a syringe, pump or another fluid source (not shown) via a Luer lock to deflate (reduce) and inflate (expand) the balloon or sheath with a thermally conductive liquid.

Figure 6A:
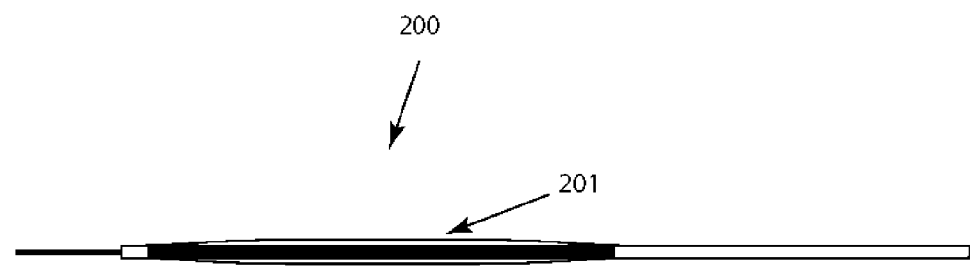
FIG. 6A is an illustration of a deflated balloon 201 that is folded for insertion into a blood vessel.
Figure 6B:
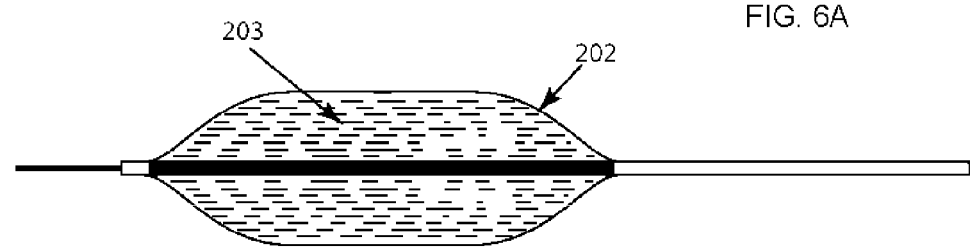
FIG. 6B is an illustration of an inflated balloon 202 with a thermally conductive liquid 203 inside.

Once the balloon catheter is fully inflated as shown for example in FIGS. 5A, and 6B, the SPLCS may run refrigerant though the multi-tubes 104. Cooling is achieved by circulating SPLC with its in initial temperature below −90 C through the multitubular section 104 that is in good thermal contact with the thermally conductive liquid 109, 203 that fills the balloon. Without being bound to theory, it is noted that the cryoablation balloon catheter transfers heat differently than the cryoprobe described in connection with FIG. 4 above. In particular, instead of directly extracting heat from the tissue as described above in connection with the cryoprobe shown in FIG. 4, the cryoablation balloon catheter of FIG. 5 transfers or extracts heat from the medium 109 used to inflate the balloon part of the catheter. By extracting heat from this medium, the entire surface of the balloon catheter serves to extract heat from the tissue. In certain applications, this is an advantage.

Figure 7A:
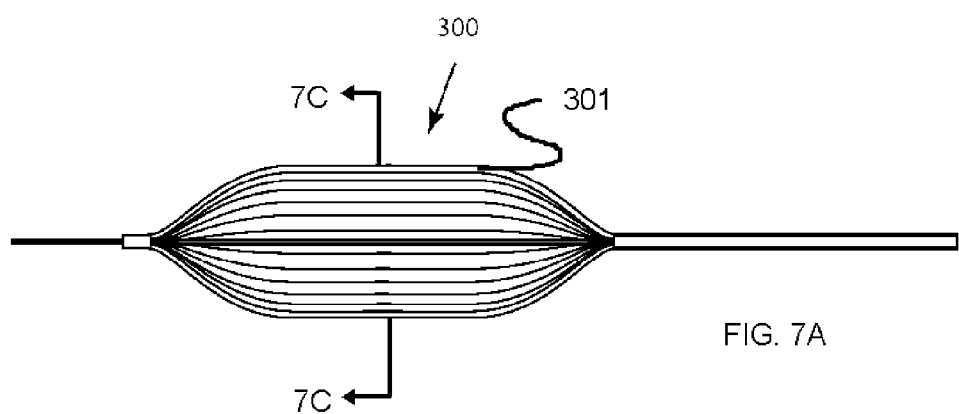
FIG. 7A is an illustration of an inflated balloon with plurality of small tubes adhered to its surface.
Figure 7B:
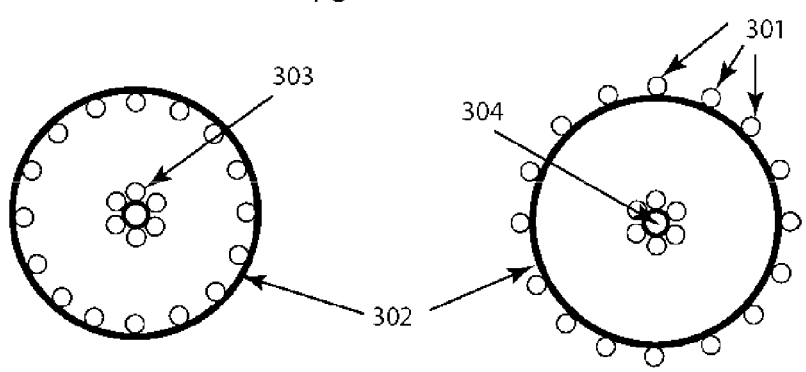
FIG. 7B is a cross sectional view of the balloon of FIG. 7A with the tubes 301 conducting the incoming flow of SPLC placed on the inner surface of the balloon 302 with the return flow of the SPLC going through the central part of the balloon 303.
Figure 7C:
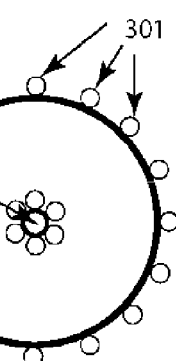
FIG. 7C is a cross sectional view of the balloon with the tubes 301 conducting the incoming flow of SPLC placed on the outside surface of the balloon 302 with the return flow of the SPLC going through the central part of the balloon 303.

FIGS. 7A-7C show another cryoablation balloon catheter 300 having microtubes 301, 303 that have refrigerant (preferably SPLC) flowing through them. However, unlike the embodiment shown in FIGS. 5-6 above, the microtubes are shown disposed (e.g., adhered) to the inside (FIG. 7B) or outside (FIG. 7C) of the balloon catheter wall 302.

The micro-tubes are preferably evenly dispersed around the perimeter or circumference of the balloon. The number of microtubes disposed around the balloon may vary widely. In one embodiment, as shown in FIG. 7C, 10-20 and more preferably 15-20 microtubes are present. In another embodiment, the number microtubes is sufficient such that a continuous layer of tubing is formed around the exterior of the outer balloon surface.

Figure 8A:
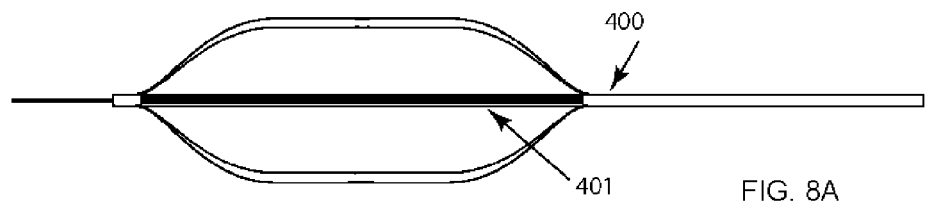
FIG. 8A is an illustration of a double balloon cryoablation balloon catheter with a multitubular cooling section inside the inner balloon.

FIG. 8A is an illustration of a double balloon cryoablation balloon catheter 400 having a multitubular inner energy delivering core 401. The energy delivering core 401 comprises one or more microtubes as described above in connection with the multitubular designs of FIG. 5.

Figure 8B:
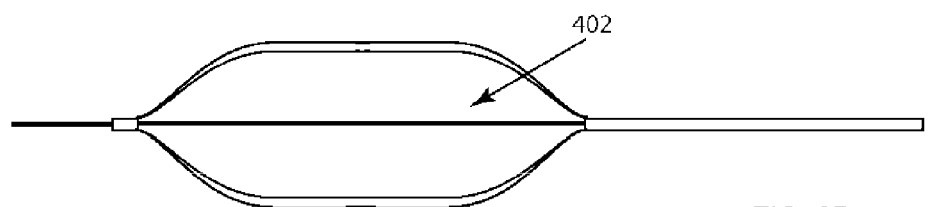
FIG. 8B is an illustration of a double balloon cryoablation balloon catheter cooled directly by SPLC 402 circulating inside the balloon.

FIG. 8B is an illustration of another double balloon cryoablation balloon catheter. However, unlike the embodiment of FIG. 8A and the use of an energy delivering core to cool a thermally conductive liquid within the balloon, the balloon is filled directly with a single phase, liquid cryogen.

Such a system may comprise a container for holding the liquid refrigerant at an initial pressure and initial temperature; a liquid pump; and the cryoablation double balloon catheter coupled to the container.

A fluid delivery lumen and a fluid return lumen extending through the elongate shaft and to the balloon members can be provided such that the balloon member is in fluid communication with the liquid refrigerant.

The balloon catheter is adapted to be expanded when liquid refrigerant is sent into the balloon member, and to be reduced in size when liquid refrigerant is withdrawn from the balloon member. Preferably the return lumen is fluidly coupled to a second container thereby completing the loop of the liquid refrigerant without the liquid refrigerant evaporating as the refrigerant is transported. In one embodiment of the invention, the containers are hand held or portable. In another embodiment, the shaft is stiff.

The double balloon may be expanded in various shapes. An example of one shape is shown in FIG. 8B.

Figure 9A:
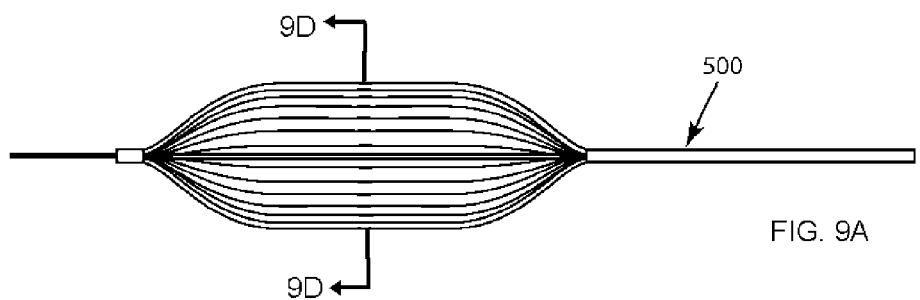
FIGS. 9A-9D are illustrations of a double balloon cryoablation balloon catheter with plurality of cooling lines adhered to the balloon walls in different configurations.
Figure 9B:
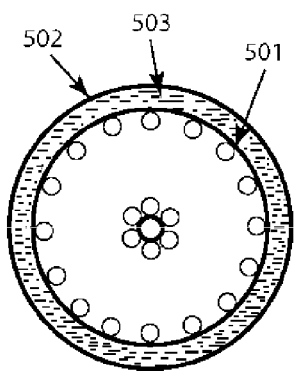
Figure 9C:
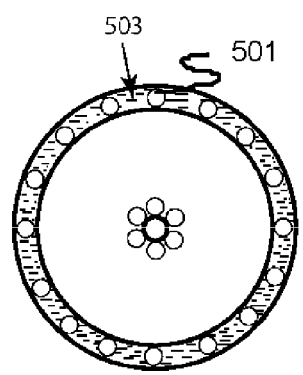
Figure 9D:
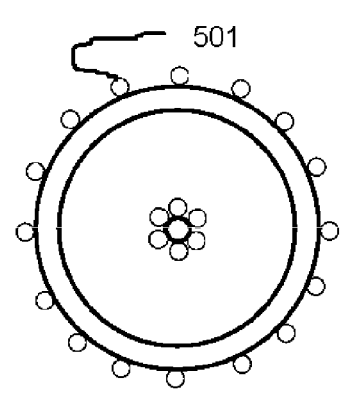

FIGS. 9A-9D show another cryoablation balloon catheter comprising two or more sheath layers. Thermal delivery micro-tubes 501 are shown disposed inside the first or inner balloon 501 (FIG. 9B) or between the walls of the first balloon 501 and the second balloon 502 (FIG. 9C). A thermally conducting liquid 503 is preferably disposed in a gap between the balloon layers. Additionally, the thermal delivery micro-tubes 501 may be disposed on the outside of the second or outer balloon member 502 (FIG. 9D). Consequently, when the balloon catheter is inflated, the micro-tubules will be pressed against the tissue directly, or with only the wall of the balloon catheter obstructing direct contact, thereby increasing cooling efficiency.

Figure 10:
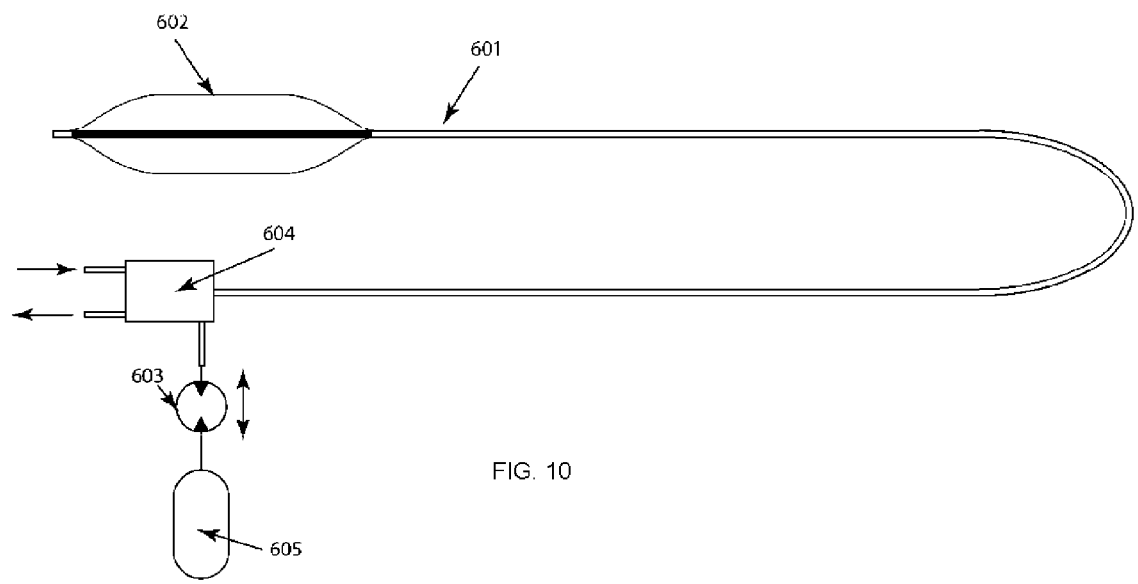
FIG. 10 is an illustration of a balloon catheter inflation system using a SPLC medium for the inflation medium.

FIG. 10 shows an inflation system of a balloon catheter 601. Inflation of the balloon is achieved by pumping a thermally conductive liquid inside the balloon 602 using a small liquid pump 603 (or syringe) attached to a designated balloon-inflation line in a connector 604. The thermally conductive liquid may be stored inside a container 605 at ambient temperature and pressure. To deflate the balloon 602, the liquid pump 603 is reversed.

The SPLC is circulated to a cryo-energy delivering core within the balloon 602 as described above. The SPLC is delivered and returned through, e.g., designated cryogen lines of connector 604.

The balloon may be made from a material that can withstand a temperature range of −200° C. to +100° C. Additionally, the balloon may be made from a material that can withstand a pressure up to 500 psi. A non-limiting example material is polyimide (Kapton® from DuPont).

Also, although the shape of the cryoablation balloon catheter 100 is shown as substantially elongate or cylindrical, and tapered, its dimensions and shape may vary greatly and as discussed further below, may be adapted for a particular application or treatment.

Figure 11A:
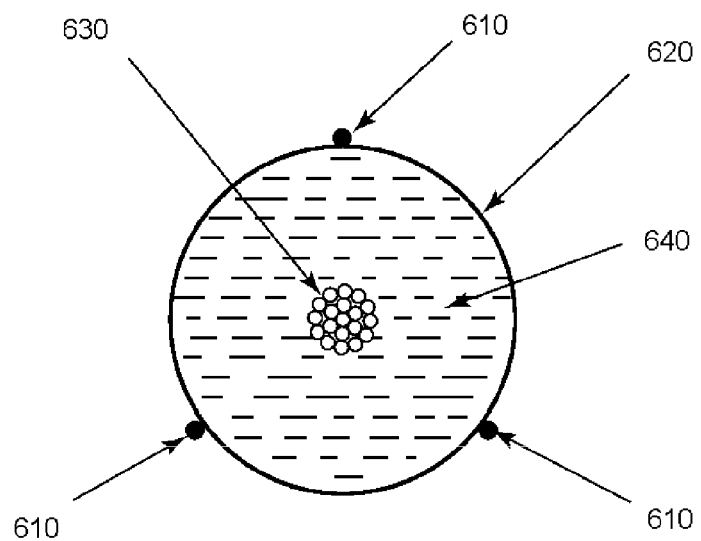
FIG. 11A is a cross section of a cryoablation balloon catheter having thermocouples on the exterior of the balloon for measuring temperature.

FIG. 11A shows cryoablation balloon setup for testing various thermally conductive liquids 640 and/or internal configurations of noted microtubules. The shown setup included a 7 mm diameter polyimide balloon 620 that has a 2.2 mm multitubular cryoprobe inside 630.

Three thermocouples 610 were attached to the outer surface of the balloon to measure its temperature as a function of time. The inner space of the balloon was filled with a thermally conductive liquid 640. The inflated balloon was then immersed in a room temperature ultrasound gel.

Figure 11B:
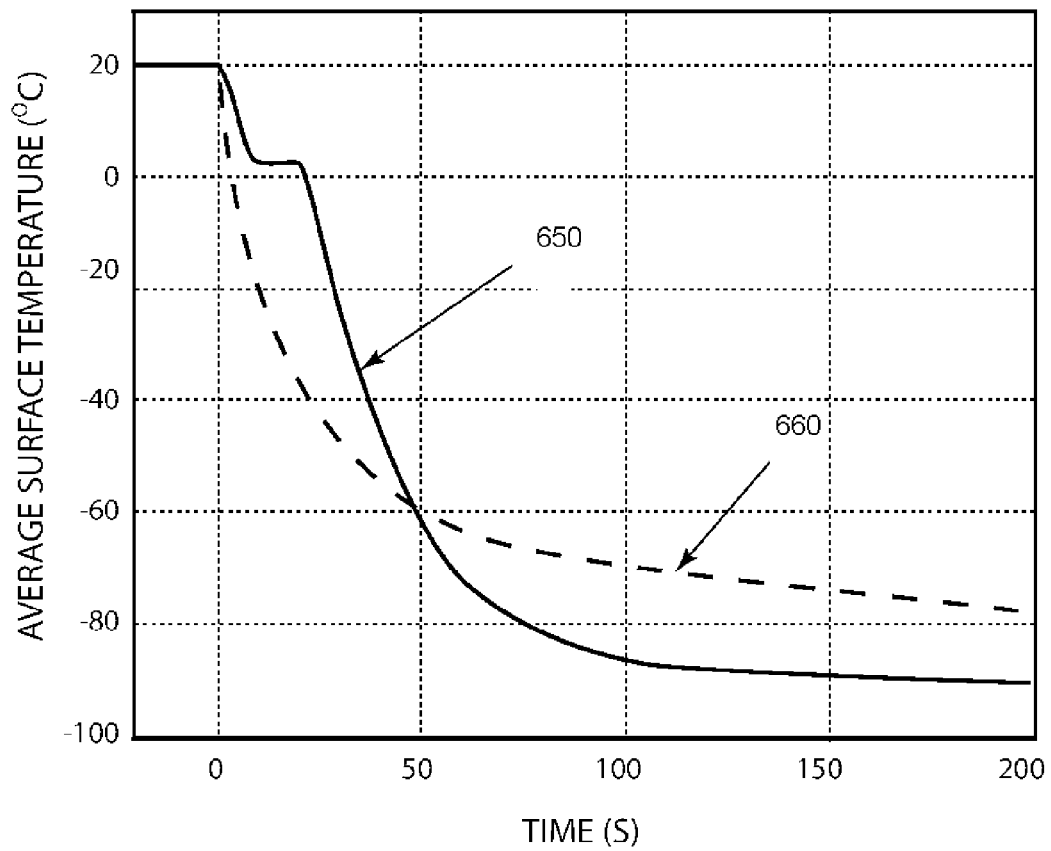
FIG. 11B is a plot indicating the temperature versus time for the balloon catheter shown in FIG. 11A for various thermally conductive mediums.

A plot is shown in FIG. 11B representing the average surface temperature (average of the three thermocouples readings) of the balloon when filled with water 660 and Gallium-Indium eutectic alloy 650 that is a liquid metal at room temperature. One can see that the liquid metal allows for faster and quicker cooling (ablation time) because after 50 seconds, the Gallium-Indium alloy continues to drop in temperature until about −90 degrees C. (about 20 degrees lower than the water 650).

The above described apparatuses have a wide variety of diagnostic and therapeutic applications including but not limited to external and internal cardiac applications, endoscopic applications, surgical tools, endovascular uses, subcutaneous and superficial dermatologic applications, radiological applications, and others.

In connection with hypertension, for example, a cryoablation balloon may be used to denervate the renal artery. The distal section of the balloon catheter is advanced through the aorta starting in the groin into the renal artery. The balloon is inflated with cold liquid which penetrates the wall of the artery and ablates/kills the nerves within and/or surrounding the wall of the artery. Cold temperatures of between −20° C. to −150° C. are applied by the catheter in either single or multiple freeze/inflation cycles to produce long-lasting the nerve destruction/non-function.

In connection with Peripheral Vascular Disease or coronary artery disease a balloon may be used in a stand-alone application (e.g., without a stent) to reopen a partially closed artery thru expansion of the balloon. In particular, a guidewire is navigated under fluoroscopy or otherwise to a target lesion. The balloon catheter may be tracked over the wire or otherwise guided to the site. The balloon tip is extended through the lesion. The balloon is expanded. The cryoballoon described herein chills the artery in a single or multiple freeze cycle to cold temperatures, in the range from −20° C. to −150° C., causing positive remodeling (i.e., bigger central lumen diameter and actual overall artery), as well as reducing or eliminating cellular and biochemical responses that result in restenosis. Additionally, the balloon could be used in conjunction with other technologies, such as a laser, that open the artery after which the described balloon is used to chill the treated section to not only prevent restenosis, but also have a "stent-like" effect.

In connection with asthma, it is thought that individuals with asthma generally have thicker muscles surrounding their airways in the lungs which result in their going into spasms/constriction easier. The above described balloon may be advanced into a passageway or bronchus within the lung, and used to freeze the bronchi or bronchial layers in the lungs to reduce the muscles themselves (i.e., cause atrophy) that result in spasms. The described balloon serves to create a deep isotherm, sufficient to result in sufficient weakening/atrophy/necrosis of the muscles. Preferably, the cryoenergy is delivered in a circumferential manner in the regions of the hyper reactive airways.

Sleep Apnea is caused by excess tissue in the throat area that gets in the way of breathing when sleeping and/or restricted or narrow air passages. Excess tissue would generally be treated by a cryo needle, but the above described balloon catheter could apply direct pressure to the soft palate as needed (see also Barrett's and ENT). In accordance with the balloon described herein, the balloon is advanced to into the throat area, expanded, and then cryoenergy applied to ablate the tissue.

Barrett's Esophagus is a pre-cancerous or cancerous growth on the wall lining of the esophagus. A cryo-balloon as described herein is advanced to the affected portion in the esophagus. The balloon is activated to freeze the affected portion of the wall to ablate/kill the unwanted growth. This serves to create the depth of ice necessary to fully ablate the growth. Balloons of various shapes may be delivered including a full 360 degree balloon in the shape of cylinder or sphere, to a slice of pie such as a half or fraction of a balloon. This allows treatment of only a portion of the circumference (e.g., 12 o'clock to 3 o'clock) by simply pressing an expandable balloon with only a quarter of its circumference getting cold, thus coming in contact with only the tissue regions needed in sparing the remaining normal tissues of the lumen circumference. The balloons may be made of a pre-shaped non distensible variation.

The above described balloon catheter may also be used to treat the Ears, Nose and Throat (ENT) disorders within the, Larynx, pharynx, nasal cavity, oral cavity, Eustachian tubes, and associated passage ways. The balloon described herein may also be used to treat growths (benign or cancerous) by ablating the tissue on the wall. Additional applications would be to open passageways. Full, hemi cylindrical/spherical, or fractional balloon configurations could allow for applying cryoenergy to a specific area, yet have a big enough surface area to cover lesions of many sizes.

In addition, these and other endoluminal balloon applications (as opposed to endovascular noted above) may be configured on a stiff shafted device, rather than a flexible catheter. In this manner, a physician may have more direct control over application of these balloons and associated placement of pressure within the required segment of the lumen.

The above described balloon catheter may also be used in Pulmonary treatment procedures such as to treat growths/spots (benign or cancerous) along walls of airways in lungs/trachea/bronchi/cartilaginous passageways and other pulmonary areas.

In connection with the bladder, there can be growths/spots on or in the wall lining of the bladder. A balloon as described herein may be advanced to the location, the balloon is expanded and used to freeze the affected portion of the wall to ablate/kill the unwanted growth. The cold energy described above serves to create the depth of ice necessary to fully ablate the growth.

There can be growths/spots on or in the wall lining of the intestinal tract. The balloon would be used to freeze the affected portion of the wall to ablate/kill the unwanted growth. This technology can create the depth of ice necessary to fully ablate the growth.

In connection with Women's Health applications including treatment of the Fallopian tubes, cervix, and uterus, a balloon can be advanced to the affected portion, and expanded. The balloon is used to treat spots, growths (benign or cancerous) by ablating the tissue on the tubes or walls as the case may be. Additional applications would be to open the tubes.

In connection with the endometrium, a balloon as described herein may be used to ablate the lining of the wall to stop excessive bleeding. This represents an alternative to a hysterectomy.

Additionally, the balloon catheter described herein may be used in connection with Veterinary Applications. The balloon is advanced to the affected or target region of the animal, the balloon is inflated, and cryoenergy is applied as described above to ablate the target. Variations of a number of the above procedures may be carried out as appropriate for the particular type of animal.

It will be understood that some variations and modification can be made thereto without departure from the spirit and scope of the present invention.

We claim:

1. A method for delivering cryoenergy to a target in a therapeutic application, the method comprising:

advancing a distal section of a balloon catheter through a lumen and to a target location in a vicinity of the target, the distal section comprising an inflatable first balloon, and said balloon catheter being in fluid communication with a coolant source;

delivering chilled coolant having an effective temperature for cryoablatinq the target to the balloon catheter;

inflating the inflatable first balloon with the chilled coolant such that the inflatable first balloon increases in size, making thermal contact with the target, and wherein the inflating step is performed while maintaining the chilled coolant, in a single phase, liquid-only state; and freezing the target by extracting heat from the target into the single phase, liquid-only coolant being transported through the inflatable first balloon thereby warming the chilled coolant; and wherein along an entire coolant flowpath extending from the coolant source, through the balloon catheter, through the inflatable first balloon in thermal contact with the target, and to at least one of the coolant source or a coolant reservoir, the chilled coolant remains in the single phase, liquid-only state and without evaporation and despite absorbing heat from the chilled coolant being introduced into the distal section in thermal contact with warm biological tissues in the therapeutic application.

2. The method of claim 1 further comprising pumping the single phase liquid-only coolant through the balloon catheter.

3. The method of claim 2 wherein the coolant source is a portable container and wherein the pumping transport the single phase liquid-only coolant from the portable container to the balloon catheter.

4. The method of claim 1 comprising withdrawing the single phase liquid-only coolant to reduce the size of the inflatable first balloon.

5. The method of claim 1 wherein the inflatable first balloon is a preset non-distensible balloon.

6. The method of claim 1 wherein the inflatable first balloon is formed of a material selected from the group consisting of polyimide, polytetrafluoroethylene, and polyethylene terephthalate.

7. The method of claim 1 further comprising surrounding the inflatable first balloon with a second balloon.

8. The method of claim 7 further comprising providing a thermally conducting liquid in a space between the inflatable first balloon and the second balloon.

9. The method of claim 1 wherein the inflatable first balloon comprises an elongate cylindrical shape having tapered ends.

10. The method of claim 1 wherein the inflatable first balloon is made of material that can withstand a temperature in a range of −200 degrees Celsius to 100 degrees Celsius.

11. The method of claim 1 wherein the step of inflating the inflatable first balloon is performed in a blood vessel.

12. The method of claim 1 wherein the chilled coolant delivered to the inflatable first balloon has a cold temperature in a range from −150 degrees Celsius to −20 degrees Celsius.

13. The method of claim 12 wherein a pressure of the chilled coolant along the entire coolant flowpath ranges from 0.4 MPa to 0.9 MPa.

14. The method of claim 13 wherein the cold temperature of the coolant along the entire coolant flowpath changes from about −150 degrees C. to about 20 degrees C.

15. The method of claim 1 wherein a temperature of the single phase, liquid-only coolant along the entire coolant flowpath increases in temperature to above −196 degrees C. without evaporation.

* * * * *